(12) United States Patent
Fujimoto et al.

(10) Patent No.: US 8,475,424 B2
(45) Date of Patent: Jul. 2, 2013

(54) DISPOSABLE PULL-ON GARMENT

(75) Inventors: Kenji Fujimoto, Nishinomiya (JP); Haruko Sato, Kobe (JP); Masato Higaki, Kobe (JP); Toshiyuki Matsuda, Akashi (JP); Hiroshi Nakahata, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 709 days.

(21) Appl. No.: 11/818,179

(22) Filed: Jun. 13, 2007

(65) Prior Publication Data
US 2007/0287975 A1 Dec. 13, 2007

Related U.S. Application Data (60) Provisional application No. 60/813,311, filed on Jun. 13, 2006.

(51) Int. Cl.
*A61F 13/15* (2006.01)
*A61F 13/20* (2006.01)

(52) U.S. Cl.
USPC ............ 604/385.13; 604/385.01; 604/385.16; 604/385.22; 604/385.23; 604/385.24; 604/385.26; 604/385.27; 604/385.28; 604/385.29; 604/385.3; 604/385.31; 604/392; 604/397

(58) Field of Classification Search
CPC ..................................................... A61F 13/551
USPC ............. 604/385.13, 385.01, 385.16, 385.22, 604/385.23, 385.24, 385.26, 385.27, 385.28, 604/385.29, 385.3, 385.31, 392, 397
See application file for complete search history.

(56) References Cited

U.S. PATENT DOCUMENTS

| 5,685,874 | A | 11/1997 | Buell et al. |
|---|---|---|---|
| 7,569,039 | B2 | 8/2009 | Matsuda et al. |
| 2002/0007148 | A1 | 1/2002 | May et al. |
| 2005/0027853 | A1 | 2/2005 | Martin et al. |
| 2005/0107763 | A1 | 5/2005 | Matsuda et al. |
| 2005/0131373 | A1 | 6/2005 | Wright et al. |
| 2005/0256489 | A1 * | 11/2005 | Sawyer et al. ........... 604/385.23 |

FOREIGN PATENT DOCUMENTS

| EP | 0526868 A | 2/1993 |
|---|---|---|
| EP | 0688550 A1 | 12/1995 |
| WO | WO 2004/006817 A | 1/2004 |

(Continued)

OTHER PUBLICATIONS

International Search Report, PCT/ISR Mail Date May 11, 2007.

*Primary Examiner* — Tatyana Zalukaeva
*Assistant Examiner* — Ginger T Chapman
(74) *Attorney, Agent, or Firm* — Thibault Fayette; Larua L. Whitmer (57) ABSTRACT

The disposable pull-on garment has a longitudinal centerline, a front region, a crotch region, and a back region. The front and back regions are joined at seams to form a waist opening and leg openings. The pull-on garment comprises a main portion, a side portion, and a waist portion. The side portion is disposed transversely outboard of the main portion. The waist portion comprises a center waist portion, an outer side waist portion, and an inner side waist portion. The contraction rate of the inner side waist portion is less than that of the center waist portion, and the contraction rate of the side portion longitudinally inboard of the inner side waist portion is greater than that of the inner side waist portion.

9 Claims, 7 Drawing Sheets

FOREIGN PATENT DOCUMENTS

| | | |
|---|---|---|
| WO | WO-2004/105664 A1 | 12/2004 |
| WO | WO-2004/105665 A1 | 12/2004 |
| WO | WO-2005/051263 A1 | 6/2005 |
| WO | WO-2005/051264 A1 | 6/2005 |

* cited by examiner

DISPOSABLE PULL-ON GARMENT

CROSS REFERENCE TO RELATED APPLICATION

This application claims the benefit of U.S. Provisional Application No. 60/813,311, filed Jun. 13, 2006, the substance of which is incorporated herein by reference.

FIELD OF THE INVENTION

The present invention relates to disposable pull-on garments which are donned by inserting the wearer's legs into the leg openings and sliding the garment up into position about the lower torso.

BACKGROUND OF THE INVENTION

Infants and other incontinent individuals wear disposable absorbent articles such as diapers to receive and contain urine and other body exudates. Absorbent garments having fixed sides (e.g., training pants or pull-on diapers) have become popular for use on children able to walk and often who are toilet training. Many disposable pull-on garments use elastic elements secured in an elastically contractible condition in the waist and/or leg openings. Typically, in order to insure full elastic fit about the leg and the waist such as is provided with durable undergarments, the leg openings and waist opening are encircled with elasticized bands of rubber or other materials positioned along the curve of the entirety of the opening.

While it may be believed that the stretchable waist opening generating high contraction force contributes to anchor the waist opening of the pull-on diapers to the wearer's body, such high contraction force sometimes actually causes sagging of the waist opening of the pull-on diaper. The front portion of the waist opening is positioned on stomach of the wearer which is considered high motion zone repeating expansion and contraction when the wearer breathes. When the stomach expands, the contraction force becomes high to generate high anchoring force. However, as the contraction force increases, the component force of the contraction force toward the crotch from the waist portion of the wearer along the surface of the wearer also increases. When such high component force is exerted on the stomach of the wearer in which the waist circumference decreases toward the crotch of the wearer, the waist portion of the pull-on diaper could sag.

In order to reduce such sagging caused by high component force exerted on the stomach, it is conceivable to remove elastic material in the front center waist portion. However, if the elastic material is removed therefrom, another drawback occurs. Namely, the front center waist portion having no contraction force can not counteract the movement of wearer. As a result, the front waist portion flips over accidentally by the wearer's movement. Such flipping-over of the waist portion is also as problematic as sagging since it gives a poor impression of the pull-on diaper to the wearer or caregiver.

Based on the foregoing, there is a need for a disposable pull-on garment to provide an improved fit around the waist opening. There is also a need for a disposable pull-on garment to improve sagging problem around the waist portion. There is also a need for a disposable pull-on garment to improve flip-over problem in the waist portion.

SUMMARY OF THE INVENTION

The present invention is directed to a disposable pull-on garment. The disposable pull-on garment has a longitudinal centerline, a front region, a crotch region, and a back region, the front region and the back region being joined at seams to form a waist opening and leg openings. The pull-on garment comprises a main portion, a side portion, and a waist portion. The side portion is disposed transversely outboard of the main portion. The waist portion comprises a center waist portion, an outer side waist portion, and an inner side waist portion. The center waist portion is disposed longitudinally outboard of the main portion. The outer side waist portion is disposed longitudinally outboard of the side portion, transversely outboard of the center waist portion, and contiguous with the seam. The inner side waist portion is disposed longitudinally outboard of the side portion, transversely inboard of the outer side waist portion, and transversely outboard of the center waist portion. The side portion is elasticized to provide elasticity and comprising a side elastic material to contract and gather at least a portion of the side portion. The waist portion is elasticized to provide elasticity and comprising a waist elastic material to contract and gather at least a portion of the waist portion. Contraction rate of the inner side waist portion is less than that of the center waist portion, and contraction rate of the side portion longitudinally inboard of the inner side waist portion is greater than that of the inner side waist portion.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). The pull-on garment is also preferably "absorbent" to absorb and contain the various exudates discharged from the body. A preferred embodiment of the pull-on garment of the present invention is the disposable absorbent pull-on garment, pull-on diaper 20, shown in FIG. 1. As used herein, the term "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.)

Figure 1:
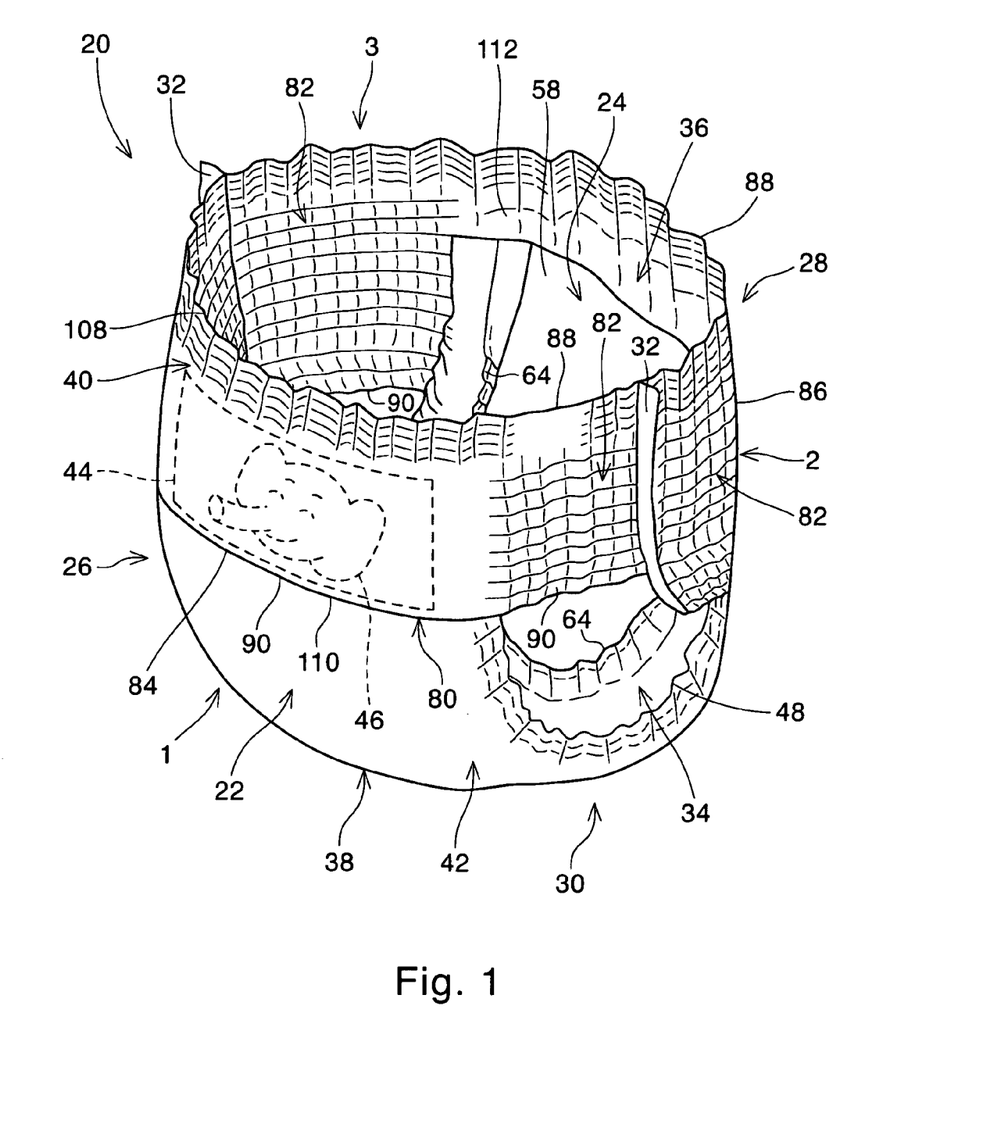
FIG. 1 is a perspective view of the disposable pull-on garment of the present invention in a typical in-use configuration.

FIG. 1 is a perspective view of the pull-on diaper 20 of the present invention. The pull-on diaper 20 has a longitudinal centerline L1 and a transverse centerline T1 (refer to FIG. 2 as well). The pull-on diaper 20 has an outer surface 22, an inner surface 24 opposed to the outer surface 22, a front region 26, a back region 28, a crotch region 30, and seams 32 which join the front region 26 and the back region 28 to form two leg openings 34 and a waist opening 36. Also referring to FIG. 3, the diaper 20 comprises a main portion 1, a side portion 2, and a waist portion 3.

In the embodiment shown in FIGS. 1 and 2, the diaper 20 comprises an absorbent main body 38 (hereinafter may be referred to as "main body") to cover the crotch region of the wearer and a belt 40 extending transversely about the waist opening 36. The diaper 20 may also comprise an outer cover layer 42 to cover the main body 38. The belt 40 defines the waist opening 36. The belt 40 and the main body 38 and/or the outer cover layer 42 jointly define the leg opening 34. Alternatively, the belt 40 and the outer cover layer 42 may jointly define the leg opening 34. The pull-on diaper 20 also has a patch sheet 44 printed with a graphic 46 thereon which may be disposed in the front region 26 and/or the back region 28.

The absorbent main body 38 absorbs and contains body exudates disposed on the main body 38. In the embodiment shown in FIG. 2, the main body 38 has a generally rectangular shape having a longitudinal centerline L2, a transverse centerline T2, left and right longitudinally extending side edges 48 (hereinafter may be referred to as "longitudinal side edge") and front and back transversely extending end edges 50 (hereinafter may be referred to as "transverse end edge"). The main body 38 also has waist panels (i.e., a front waist panel 52 positioned in the front waist region 26 of the diaper 20 and a back waist panel 54 positioned in the back waist region 28) and a crotch panel 56 in the crotch region 30 between the front and back waist panels 52, 54.

The belt 40 comprises a front belt 84 and a back belt 86 (hereinafter may be referred to as "front and back belt 84, 86) and has a ring-like configuration by connecting the front belt 84 and the back belt 86 at the seams 32. Each of the front belt 84 and the back belt 86 has a central panel 80F, 80B and side panels 82F, 82B contiguous with the central panel 80F, 80B and extending transversely outwardly from the central panel 80F, 80B. Thus, the belt 40 comprises a central panel 80F, 80B and the side panels 82F, 82B. Herein, a portion of a front member and a portion of a back member may be indicated by a reference number with "F" suffix and "B" suffix, respectively, as necessary. Therefore, the "central panel 80F, 80B" for example indicates the "front central panel 80F" and the "back central panel 80B". The "central panel 80" also may mean the "front central panel 80F" and the "back central panel 80B".

Each of the front belt 84 and the back belt 86 has a transversely extending distal edge 88F, 88B, a transversely extending proximal edge 90F, 90B, and longitudinally extending left and right side edges 89F, 89B. Herein, the term "proximal" is used to indicate the position of a "proximal" portion being closer relative to the crotch panel of the main body than the position of a "distal" portion. Therefore, the proximal edge 90F, 90B is located closer than the distal edge 88F, 88B relative to the crotch panel 56 of the main body 38. The front and back belts 84, 86 are joined at or adjacent to the side edges 89F, 89B at the seams 32 to form a pull-on diaper having a waist opening 36 and two leg openings 34. The front central panel 80F may partly or entirely overlap with the front waist panel 52 of the main body 38. The back central panel 80B may partly or entirely overlap with the back waist panel 54 of the main body 38. However, the central panel 80F, 80B does not extend into the crotch panel 56 of the main body 38 and is not disposed in the crotch panel 56. In the embodiment shown in FIG. 2, the central panel 80F, 80B partly overlaps with and is joined to the front waist panel 52 and the back waist panel 54, respectively.

Figure 4:
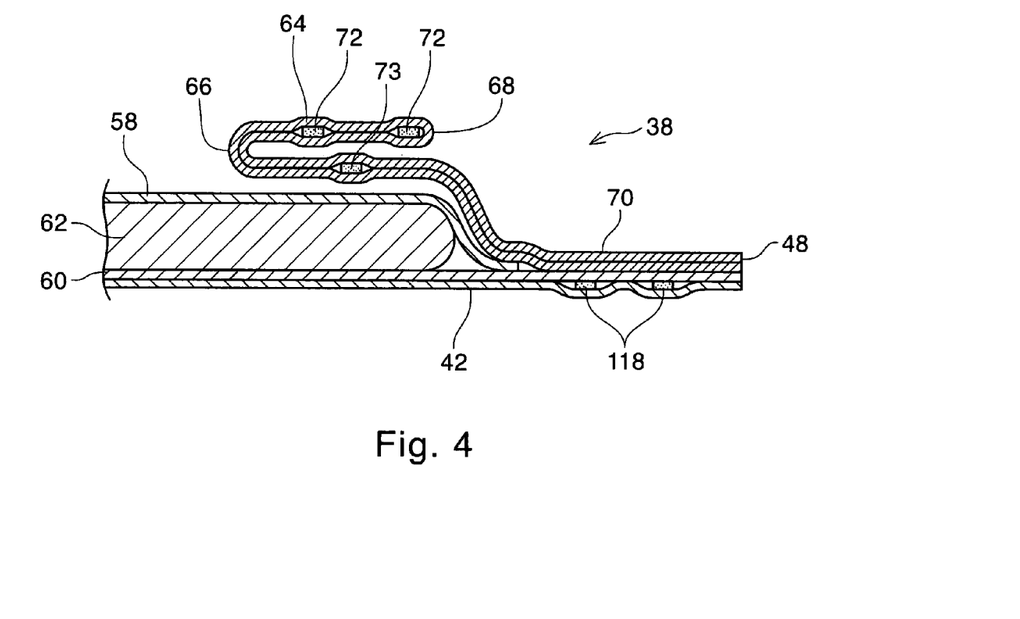
FIG. 4 is a cross-sectional view of FIG. 2 taken along the line IV-IV.
Figure 5:
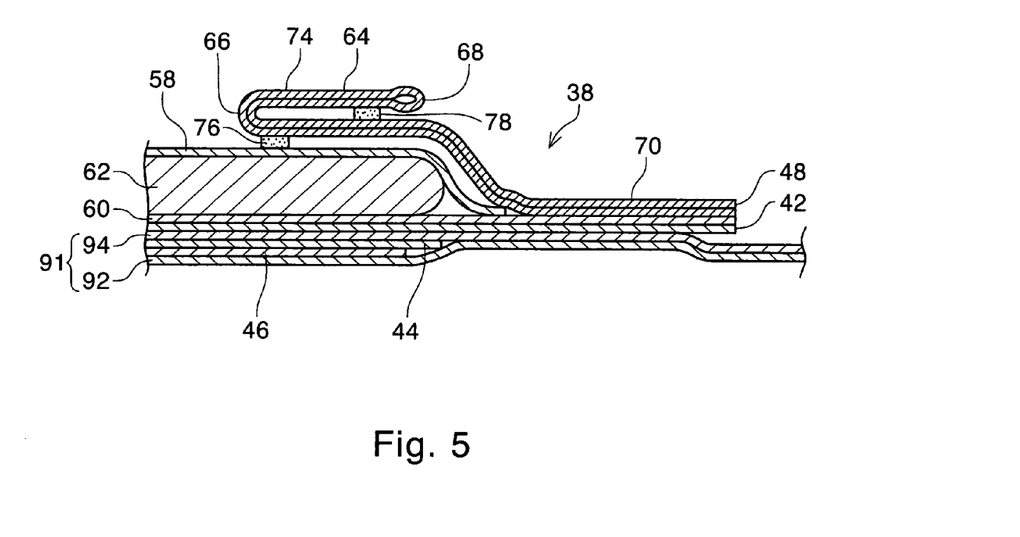
FIG. 5 is a cross-sectional view of FIG. 2 taken along the line V-V.
Figure 6:
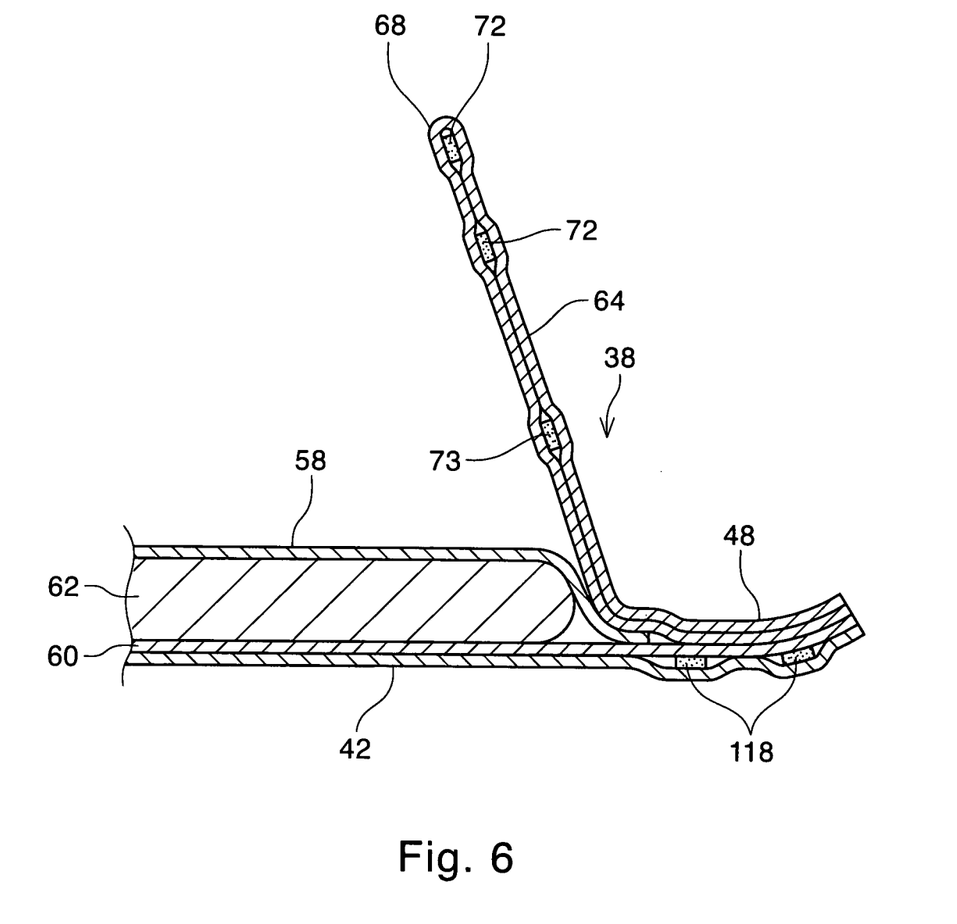
FIG. 6 is a cross-sectional view showing a typical in-use configuration of the portion shown in FIG. 4.

The main body 38 comprises a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 4 comprises a single layer of material which is folded into two layers. The barrier leg cuff 64 extends from the longitudinal side edge 48 toward the longitudinal centerline L2 and then is folded along the folding line 66 back toward the longitudinal side edge 48. The barrier leg cuff 64 has two barrier cuff elastic materials 72 adjacent to the distal portion 68 and one barrier cuff elastic material 73 adjacent to the proximal portion 70 of the barrier leg cuff 64. The proximal portion 70 of the barrier leg cuff 64 is joined to the backsheet 60 adjacent to the longitudinal side edge 48. The portion of the barrier leg cuff 64 along the folding line 66 and the distal portion 68 are free from attachment to any portion of the main body 38 in the crotch panel 56 such that the barrier leg cuff 64 stands up toward the wearer's body as shown in FIG. 6 when the diaper 20 is used. The transverse end 74 of the barrier leg cuff 64 is joined to the topsheet 58 adjacent to the folding line 66 by an attachment means 76 which may be any known means such as an adhesive and is joined onto the barrier leg cuff 64 itself along the distal portion 68 by an attachment means 78 which may be any known means such as an adhesive as shown in FIG. 5.

The liquid pervious topsheet 58 is preferably positioned adjacently the body-facing surface of the absorbent core 62 and may be joined thereto and/or to the backsheet 60 by any attachment means known in the art. The liquid impervious backsheet 60 is generally that portion of the diaper 20 positioned adjacently the garment-facing surface of the absorbent core 62 and prevents the exudates absorbed and contained therein from soiling articles that may contact the diaper 20. The absorbent core is positioned between the topsheet 58 and the backsheet 60 and absorbs and retains liquids such as urine and other certain body exudates. The topsheet 58, the backsheet 60 and the absorbent core may be manufactured any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet. Suitable absorbent core materials may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The outer cover layer 42 is disposed on the outer surface 22 of the diaper 20 and covers the crotch panel 56 of the absorbent main body 38. The outer cover layer 42 may extend into and cover the front waist panel 52 and the back waist panel 54 of the main body 38. The outer cover layer 42 is directly joined to and covers the liquid impervious backsheet 60 of the main body 38. The central panel 80 of the front and back belt 84, 86 portion is joined to the front waist panel 52 and the back waist panel 54 of the main body 38 through the outer cover layer 42. Thus, the outer cover layer 42 is sandwiched between the front and back belt 84, 86 and the liquid impervious backsheet 60 of the main body 38. In the embodiment shown in FIGS. 2 and 4, the outer cover layer 42 is coextensive with the liquid impervious backsheet 60. The leg elastic material 118 is disposed so as to extend generally longitudinally along the longitudinal side edge 48 of the main body 38. The leg elastic material 118 may be disposed at least in the crotch region 30 of the diaper 20 or may be disposed along the entirety of the longitudinal side edge 48.

The outer cover layer 42 comprises a material separate from the material of the inner layer 94 and the outer layer 92 constituting the belt 40. The outer cover layer 42 may comprise two or more layer of materials. The outer cover layer 42 may comprise any known materials and may comprise materials as used for the front and back belt 84, 86 as explained above. Preferably the outer cover layer 42 comprises a single layer of nonwoven web of synthetic fibers. More preferably, the outer cover layer 42 comprises a single layer of hydrophobic, non-stretchable nonwoven material.

Figure 7:
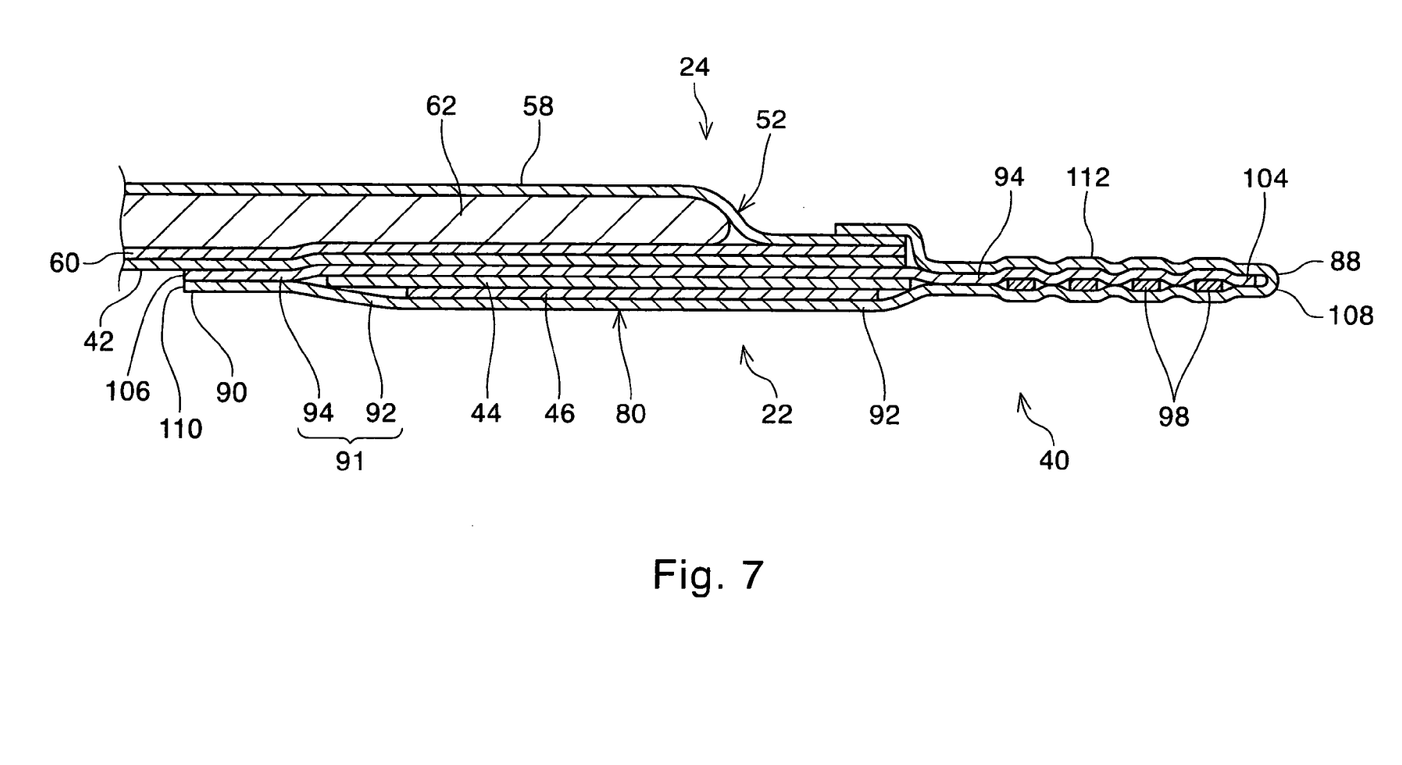
FIG. 7 is a cross-sectional view of FIG. 2 taken along the line VII-VII.

The belt 40, may be ring-like and elastic. The ring-like elastic belt 40 extends transversely about the waist opening 36 of the diaper 20 and acts to dynamically create fitment forces and to distribute the forces dynamically generated during wear. The ring-like elastic belt 40 comprises a belt layer 91 including an outer layer 92. The belt layer 91 may further comprise an inner layer 94. A belt elastic material 96 is interposed between the outer layer 92 and the inner layer 94. The front belt 84 and the back belt 86 may comprise the same materials and/or may have the same structure. Alternatively, the front belt 84 and the back belt 86 may comprise different materials and/or may have different structures. In the embodiment of FIG. 2, the front belt 84 and the back belt 86 generally have the same layer structure. Referring to FIG. 7, the inner layer 94 has a transversely extending distal end 104 and a transversely extending proximal end 106. The outer layer 92 has a transversely extending distal end edge 108 and a transversely extending proximal end edge 110. The inner layer 94 is almost coextensive with the contour of the front and back belt 84, 86. Alternatively, the inner layer 94 may be smaller than the size of the front and back belt 84, 86. The outer layer 92 of the belt layer 91 is longer than the size of the inner layer 94 in the longitudinal direction and an end flap 112 of the outer layer 92 is folded to cover the distal end 104 of the inner layer 94 at the waist opening 36 and to form a distal end edge 108 of the outer layer 92. The inner layer 94 of the belt layer 91 may also have an end flap which may be folded together with the end flap 112 of the outer layer 92. The end flap of the inner layer 94 may be longer or shorter than or equal to the end flap of the outer layer 92. Alternatively, the end flap 112 may be eliminated such that the outer layer 92 terminates at the waist opening 36 to form the distal end edge 108. In the embodiment shown in FIGS. 2 and 7, the distal end edge 108 and the proximal end edge 110 of the outer layer 92 correspond to the distal edge 88 and the proximal edge 90 of the front and back belt 84, 86, respectively. The outer layer 92 surrounded by the distal end edge 108 and the proximal end edge 110 define the shape of the front and back belt 84, 86 in the embodiment shown in FIGS. 2 and 7.

The front and back belt 84, 86 may comprise any known materials. Suitable material for the front and back belt 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. Preferably the belt comprises a nonwoven web of synthetic fibers. The belt may comprise a stretchable nonwoven. More preferably, the belt comprises an inner hydrophobic, non-stretchable nonwoven material and an outer hydrophobic, non-stretchable nonwoven material.

The belt elastic material 96 comprises a waist elastic material 98 and a side elastic material 100. The waist elastic material 98 may comprise one or more of elastic elements such as strands or panels extending in the transverse direction. The side elastic material 100 also may comprise one or more of elastic elements such as strands or panels extending in the transverse direction. In the embodiment shown in FIG. 2, the waist elastic material 98 and the side elastic material 100 comprise a plurality of elastic strands which are disposed at a constant interval in the longitudinal direction. Alternatively, the waist elastic material 98 and the side elastic material 100 may be disposed at a different interval in the longitudinal direction. The waist elastic material 98 is disposed along the distal edge 88 of the front and back belt 84, 86. The side elastic material 100 is disposed in the side panel 82 of the front and back belt 84, 86. No elastic material may be provided in a portion of the central panel 80 of the front and back belt 84, 86 which overlaps with the absorbent core 62, preferably with the front and back waist panel 52, 54 of the main body 38.

Figure 2:
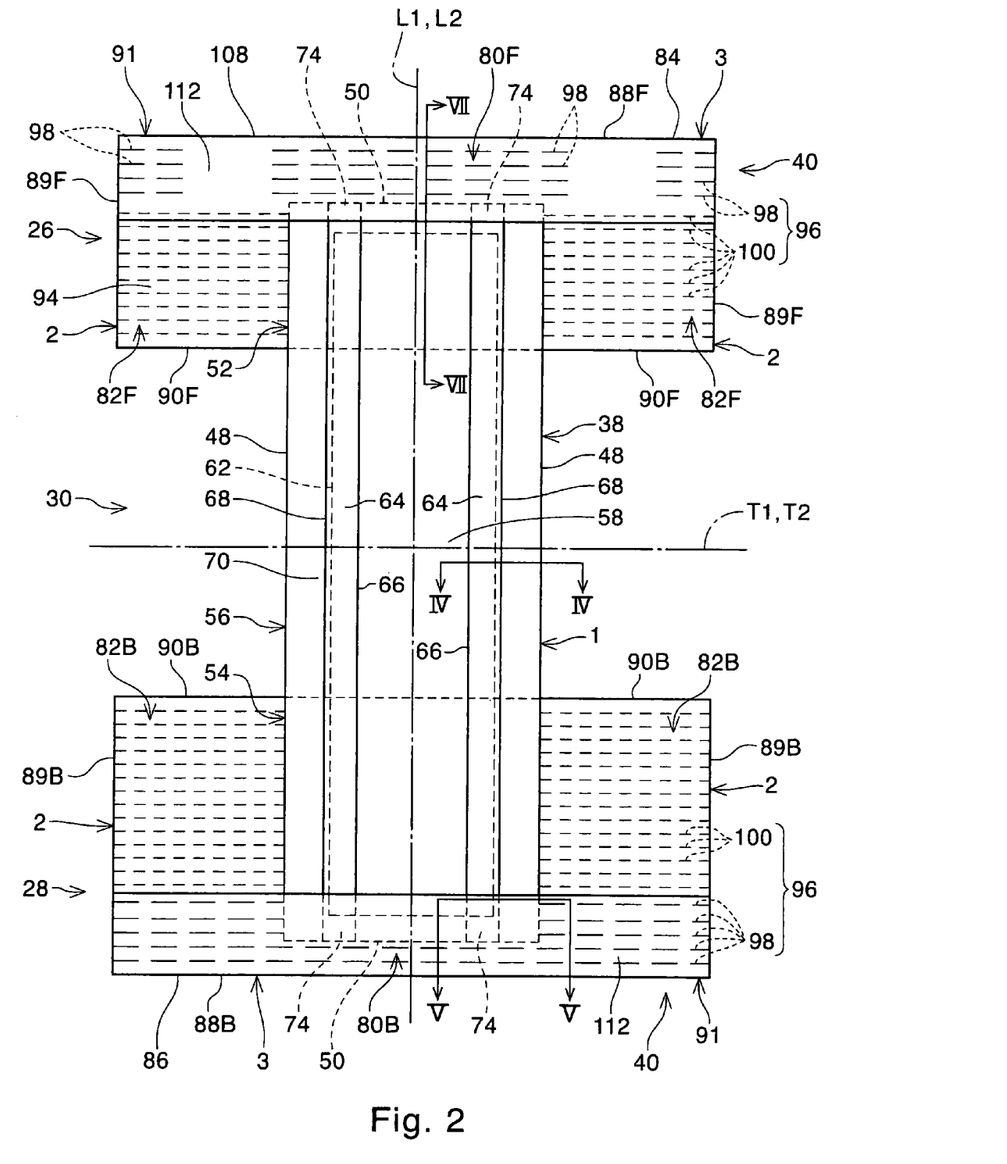
FIG. 2 is a plan view of the pull-on garment in its flat uncontracted condition showing the inner surface.
Figure 3:
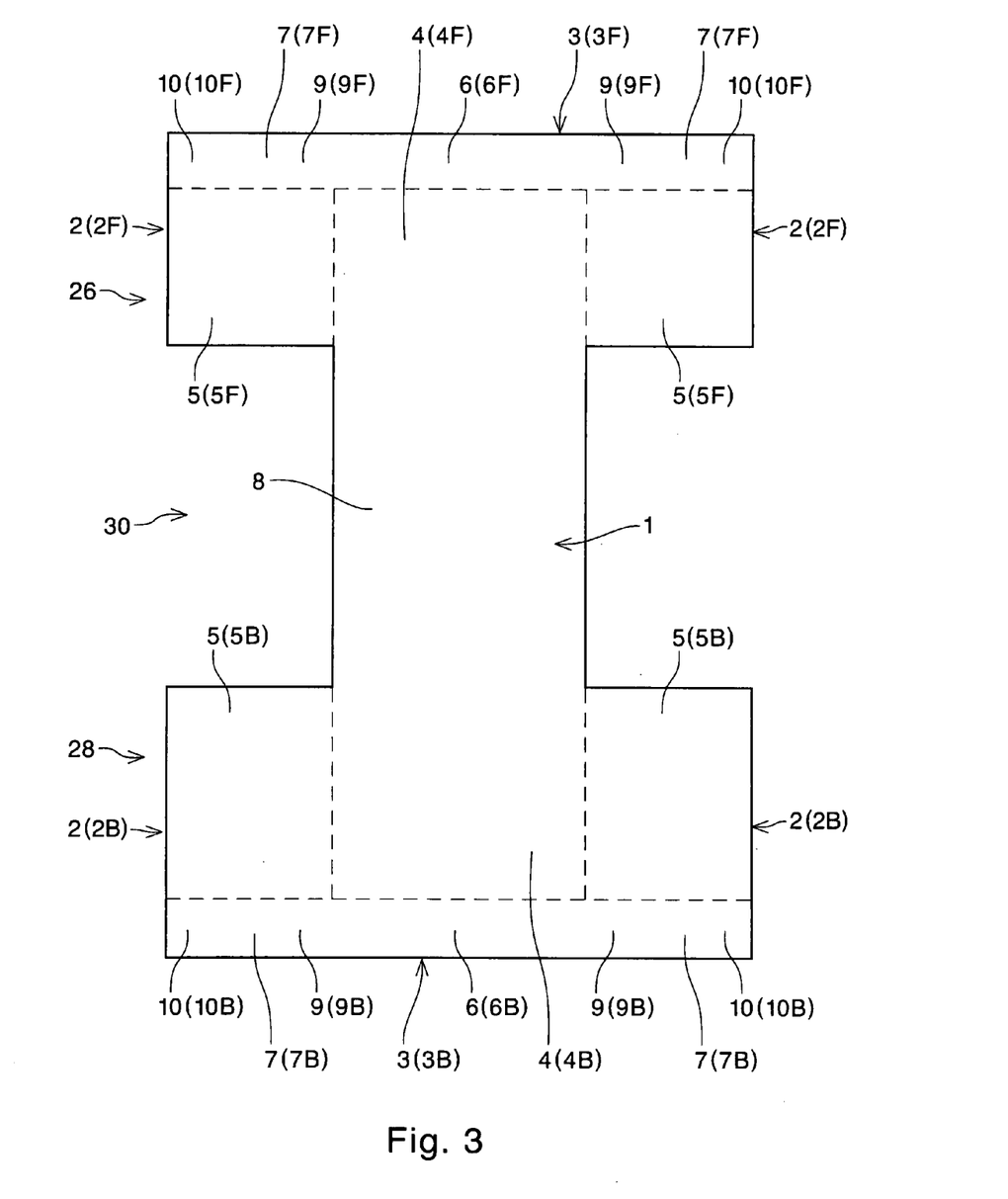
FIG. 3 is a schematic plan view of the pull-on garment in its flat uncontracted condition showing the main portion, the side portion, and the waist portion.

Referring to FIG. 3, the main portion 1 extends longitudinally along the longitudinal centerline L1 (shown in FIG. 2) from the front region 26 through the crotch region 30 to the back region 28. The main portion 1 comprises a front waist main portion 4F, a back waist main portion 4B, and a crotch main portion 8 therebetween. The side portion 2 comprises a front side portion 5F and a back side portion 5B. The side portion 2 is disposed transversely outboard of the main portion 1. More specifically the front side portion 5F is disposed transversely outboard of the front waist main portion 4F, and the back side portion 5B is disposed transversely outboard of the back waist main portion 4B. The waist portion 3 comprises a front center waist portion 6F, a back center waist portion 6B, a front side waist portion 7F, and a back side waist portion 7B. The center waist portion 6 is disposed longitudinally outboard of the waist main portion 4. The side waist portion 7 is disposed longitudinally outboard of the side portion 5 and disposed transversely outboard of the center waist portion 6. The side waist portion 7 further comprises a front outer side waist portion 10F, a back outer side waist portion 10B, a front inner side waist portion 9F, and a back inner side waist portion 9B. The outer side waist portion 10 is disposed contiguous with the seam 32 (refer to FIG. 1). The inner side waist portion 9 is disposed transversely inboard of the outer side waist portion 10 and transversely outboard of the center waist portion 6. Herein, the term "longitudinally outboard of" or "longitudinally inboard of" means that an object portion is disposed further or closer, respectively, with respect to the transverse centerline T1 than a fiducial portion. Herein, the term "transversely outboard of" or "transversely inboard of" means that an object portion is disposed further or closer, respectively, with respect to the longitudinal centerline L1 than a fidual portion. By way of example, the side portion 2 disposed transversely outboard of the main portion 1 means the side portion 2 disposed further than the main portion 1 with respect to the longitudinal centerline L1.

The main portion 1, the side portion 2, and the waist portion 3 may be formed with separate elements. For example, separate elements of the main portion 1, the side portion 2 and the waist portion 3 may be joined by any known means to each other, e.g., along the dotted line shown in FIG. 3. Alternatively, at least two of or all of the main portion 1, the side portion 2 and the waist portion 3 may be formed with a single piece of material. For example, the diaper 20 may comprise a single piece of chassis layer such as a nonwoven backsheet layer extending into the main portion 1, the side portion 2 and the waist portion 3 to provide a uni-body of the diaper 20. In the embodiment shown in FIGS. 1, 2 and 3, the main portion 1 comprises the waist panels 52, 54 of the main body 38, the crotch panel 56 of the main body 38, and a portion of the central panel 80F, 80B of the belt 40. The main portion 1 may further comprise a portion of the outer cover layer 42. The side portion 2 comprises a portion of the side panel 82 of the belt 40. The center waist portion 6 comprises a portion of the central panel 80 of the belt 40. The side waist portion 7 comprises a portion of the side panel 82 of the belt. Alternatively, the side portion 2 may comprise a portion of the main body 38. Further, the center waist portion 6 and/or the side waist portion 7 may comprise a portion of the main body 38.

A portion of or the entirety of the waist portion 3 is elasticized to provide elasticity along the waist opening 36 in the transverse direction of the diaper 20. The waist portion 3 comprises the waist elastic material 98 to provide contraction force to contract and gather at least a portion of the waist portion 3. A portion of or the entirety of the side portion 2 is elasticized to provide elasticity in the transverse direction of the diaper 20. The side portion 2 comprises the side elastic material 100 to provide contraction force to contraction and gather at least a portion of the side portion 2.

In the present invention, the waist portion 3 is rendered to have different contraction rate along the waist opening 36 of the diaper 20. More specifically, the contraction rate of the inner side waist portion 9 is less than that of the center waist portion 6. The contraction rate of the outer side waist portion 10 may be greater than that of the inner side waist portion 9. Alternatively, the contraction rate of the outer side waist portion 10 may be the substantially same as that of the inner side waist portion 9. Further, the contraction rate of the outer side waist portion 10 may be the substantially same as that of the center waist portion 6, may be greater than that of the center waist portion 6, or may be less than that of the center waist portion 6.

Herein, contraction rate is determined by the ratio of a shortened length of a portion to a stretched length of a portion. For example, the center waist portion 6 has a stretched center waist length and a contracted center waist length. The stretched center waist length is the length of the center waist portion 6 measured when the center waist portion 6 is fully stretched out against the contraction force of the waist elastic material 98. The contracted center waist length is the length measured when the center waist portion 6 is contracted by the contraction force of the waist elastic material 98. Therefore, the center waist portion 6 is typically stretchable from the contracted center waist length up to the stretched center waist length. When the center waist portion 6 is elasticized by joining the pre-stretched waist elastic material 98 thereto, the stretched center waist length is normally the stretched length of the materials such as a nonwoven or a polyfilm constituting the center waist portion 6, and the contracted center waist length is normally the length of the center waist portion 6 gathered by relaxing the waist elastic material 98. The shortened length of the center waist portion 6 is obtained by the formula; (shortened center waist length)=(stretched center waist length)−(contracted center waist length). The contraction rate of the center waist portion 6 is obtained by the formula; (contraction rate)=(shortened center waist length)/(stretched center waist length). By way of example, when the center waist portion 6 has a stretched center waist length of 10 cm and a contracted center waist length of 6 cm, the shortened center waist length is 4 cm and the contraction rate of the center waist portion 6 is 0.4 (i.e., 40%). Likewise, the inner side waist portion 9 has a stretched inner side waist length and a contracted inner side waist length, and the contraction rate of the inner side waist portion 9 is obtained by the formula; (contraction rate)=(shortened inner side waist length)/(stretched inner side waist length). The outer side waist portion 10 has a stretched outer side waist length and a contracted outer side waist length, and the contraction rate of the outer side waist portion 10 is obtained by the formula; (contraction rate)=(shortened outer side waist length)/(stretched outer side waist length).

The side portion 2 is also rendered to have different contraction rate from a portion of the waist portion 3. The contraction rate of the side portion 2 longitudinally inboard of the inner side waist portion 9 is greater than the inner side waist portion 9. The side portion 2 longitudinally inboard of the inner side waist portion 9 has a stretched side length and a contracted side length, and the contraction rate of the side portion 2 is obtained by the formula; (contraction rate)=(shortened side length)/(stretched side length). The entirety of the side portion 2 may have greater contraction rate than the inner side waist portion 9.

Figure 8:
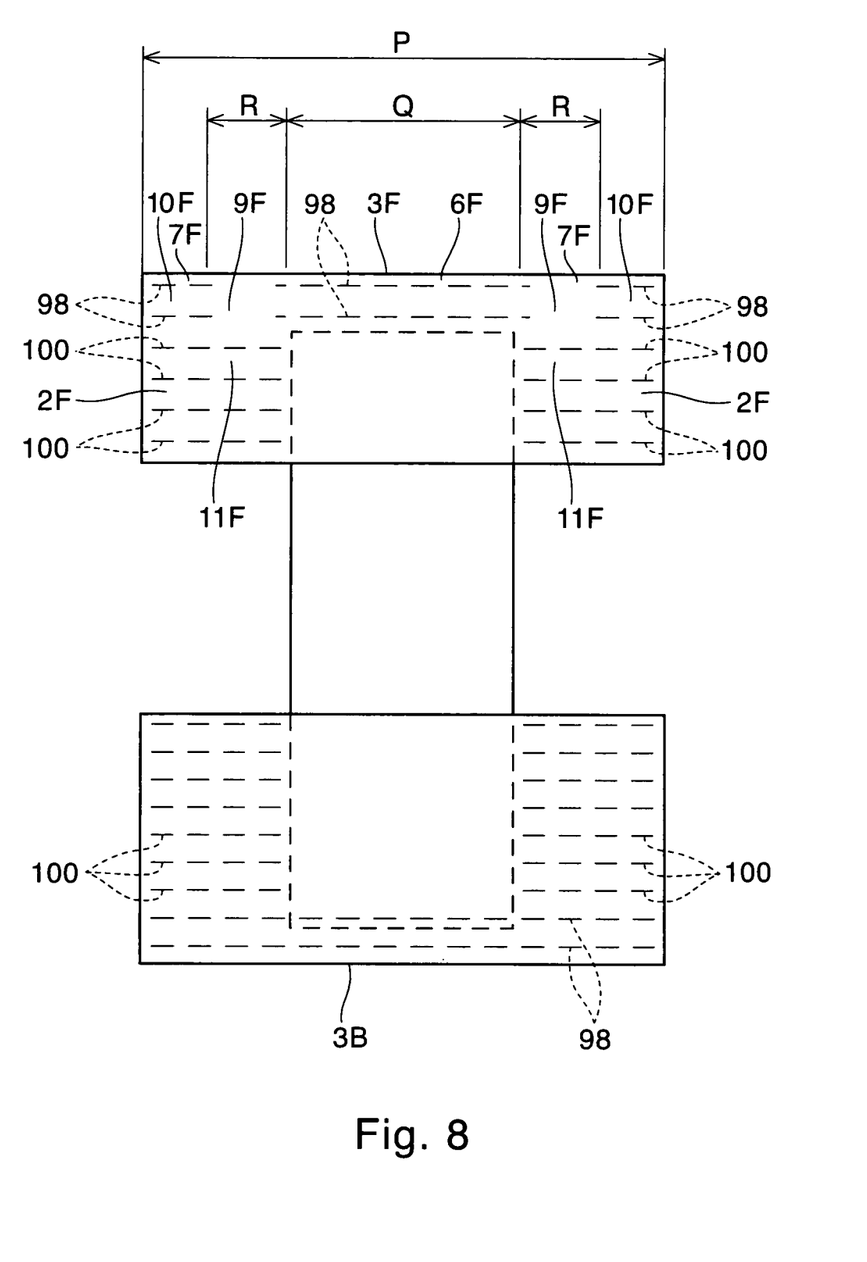
FIG. 8 is a schematic plan view of the garment of the present invention in its flat uncontracted condition showing the outer surface.

In the embodiment shown in FIGS. 1, 2 and 3, the waist portion 3 is elasticized in a portion thereof by selectively providing the waist elastic material 98. Referring to FIG. 8 as well, the waist elastic material 98 is provided in the entirety of the front center waist portion 6F and in a portion of the front side waist portion 7F. In the front side waist portion 7F, the waist elastic material 98 is provided in the entirety of or the majority portion of the front outer side waist portion 10F, but not provided in the entirety of or the majority portion of the front inner side waist portion 9F. The waist elastic material 98 is also provided in the entirety of the back waist portion 3B. In the embodiment, the waist elastic material 98 of the front center waist portion 6F, the front outer side waist portion 10F and the back waist portion 3B is pre-stretched up to the same extensibility rate to provide the substantially same contraction rate. For example, the waist elastic material 98 may be pre-stretched up to between about 130% and about 400% of its relaxed, untensioned length (When the elastic material is stretched to, e.g., 150%, the elastic material having a relaxed, untensioned length of 10 cm is stretched to 15 cm.). Since no elastic material is joined in the front inner side waist portion 9F, the contraction rate in the front inner side portion 9F is rendered substantially zero such that the contraction of the front inner side waist portion 9F is substantially zero. Thus, the contraction rate of each portion can be adjusted by selectively providing the elastic material to each portion.

In the embodiment shown in FIGS. 1, 2 and 3, the entirety of the front side portion 2F is elasticized by providing the side elastic material 100. As the result, a portion 11F (refer to FIG. 8) of the side portion 2F which is longitudinally inboard of the front inner side waist portion 9F is contracted by the side elastic material 100.

The contraction rate of each portion can be adjusted by any alternative methods. Selectively providing the elastic material for the portion which requires contraction while providing no elastic material for the portion which requires no contraction is one method to adjust the contraction rate for each portion. Instead, the elastic material such as the waist elastic material 98 may be provided along the entirety of the waist opening 36 and may be subsequently cut to eliminate or reduce the contraction force of the elastic material. To adjust the contraction rate, it is also possible to adjust the rate of pre-stretch of the elastic material when the elastic material is joined to each portion. Further, it is possible to change the properties of elastic material, such as material, number, width, or caliper of the elastic material.

While the contraction rate of each portion in the front region 26 is adjusted in the embodiment shown in FIGS. 1, 2 and 3, the contraction rate of each portion in the back region 28 may be also adjusted if so desired.

As explained above, the contraction rate of the inner side waist portion 9 is less than that of the center waist portion 6. Since the contraction rate of the center waist portion 6 is relatively high, the center waist portion 6 provides stretchability to the waist portion 3. In contrast, since the contraction rate of the inner side waist portion 9 is relatively low, the contracted inner side waist length is close to or the almost same as the stretched inner side waist length. It preliminarily increases the waist circumference of the diaper 20. Therefore, the center waist portion 6 does not need to be stretched excessively in use. As the result, the contraction force of the center waist portion 6 decreases and the component force toward the crotch from the waist portion also decreases. It helps to improve the sagging problem of the diaper and the flipping-over problem of the center waist portion 6. Further, the contraction rate of the side portion 2 (which corresponds to the low motion zone of wearer's body) longitudinally inboard of the inner side waist portion 9 is greater than that of the inner side waist portion 9. Since the contraction rate of the side portion 2 longitudinally inboard of the inner side waist portion 9 is relatively high, the contraction force in the side portion 2 increases to support the waist portion 3, specifically to support the inner side waist portion 9 in which the contraction force is relatively low. It improves fit performance of the diaper 20. Additionally, when the contraction rate of the outer side waist portion 10 is greater than that of the inner side waist portion 9, the outer side waist portion 10 counteracts the stretching force and prevents the stretching force being directly transmitted to the side seam 32. It prevents the side seam from tearing when the waist portion 3 is extended for application of the diaper 20 to the wearer.

In order to enhance the benefits of the present invention, the contraction rate of the inner side waist portion 9 is less than about 10%. It may be less than about 5%, or may be less than about 3%. The contraction rate of the center waist portion 6 is more than about 40%. It may be more than about 60%, or may be more than about 80%. The contraction rate of the side portion 2 longitudinally inboard of the inner side waist portion 9 is more than about 40%. It may be more than about 60%, or may be more than about 80%. The waist portion 3 has a stretched waist length P between the left and right seams 32, and the center waist portion 6 has a stretched center waist length Q. The stretched center waist length Q may be between about 45% and about 85% of the stretched waist length P. Each of the left and right inner side waist portion 9 oppositely disposed transversely outboard of the center waist portion 6 has a stretched inner side waist length R. Each of the left and right stretched inner side waist length R may be between 5% and about 25% of the stretched waist length P.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable pull-on garment having a longitudinal centerline, a front region, a crotch region, and a back region, the front region and the back region being joined at seams to form a waist opening and leg openings, the pull-on garment comprising:
    a) an absorbent main body defining a main portion, said absorbent main body comprising a liquid pervious topsheet, a liquid impervious backsheet and an absorbent core disposed between said topsheet and said backsheet, said absorbent main body having longitudinal side edges and front and back end edges; and
    b) a belt having transverse distal and proximal edges, said belt defining a side portion, and a waist portion, wherein the side portion is disposed transversely outboard of the main portion, the waist portion comprising a center waist portion, an outer side waist portion, and an inner side waist portion, wherein the center waist portion is disposed longitudinally outboard of the main portion, wherein the outer side waist portion is disposed longitudinally outboard of the side portion, transversely outboard of the center waist portion, and contiguous with the seamand wherein the inner side waist portion is disposed longitudinally outboard of the side portion, transversely inboard of the outer side waist portion, and transversely outboard of the center waist portion,
    wherein the side portion is elasticized to provide transverse elasticity and comprises a side elastic material to contract and gather at least a portion of the side portion,
    wherein the waist portion is elasticized to provide elasticity and comprises a waist elastic material to contract and gather at least a portion of the waist portion, wherein the center waist portion, the inner side waist portion, the outer side waist portion and the side portion each have a contraction rate, wherein the contraction rate of the inner side waist portion is less than the contraction rate of the center waist portion, the contraction rate of the outer side waist portion is greater than the contraction rate of the inner side waist portion and the contraction rate of the side portion longitudinally inboard of the inner side waist portion is greater than the contraction rate of the inner side waist portion and wherein the absorbent main body is joined to said belt such that said front and back edges of said absorbent main body are disposed inboard of said transverse distal edge of said belt.

2. The disposable pull-on garment of claim 1 wherein the contraction rate of the inner side waist portion is less than about 10%.

3. The disposable pull-on garment of claim 1 wherein the contraction rate of the inner side waist portion is substantially zero.

4. The disposable pull-on garment of claim 1 wherein the waist portion has a stretched waist length between the seams and the center waist portion has a stretched center waist length, and the stretched center waist length is between about 45% and about 85% of the stretched waist length.

5. The disposable pull-on garment of claim 4 wherein the inner side waist portion has a stretched inner side waist length, and the stretched inner side waist length is between about 5% and about 25% of the stretched waist length.

6. The disposable pull-on garment of claim 1 wherein the absorbent main body comprises waist panels and a crotch panel between the waist panels, the belt comprises a central panel and side panels extending transversely outwardly from the central panel, wherein the main portion comprises the waist panel, the crotch panel, and the central panel; the side portion comprises the side panel; the center waist portion comprises the central panel; and the side waist portion comprises the side panel.

7. A disposable pull-on garment having a longitudinal centerline, a front region, a crotch region, and a back region, the front region and the back region being joined at seams to form a waist opening and leg openings, the pull-on garment comprising:

a main portion comprising a liquid pervious backsheet, a liquid impervious backsheet and an absorbent core disposed between the liquid pervious topsheet and the liquid impervious backsheet, said main portion having left and right longitudinal side edges and front and back end edges and said absorbent core having left and right longitudinal side edges and front and back transverse edges;

a left elasticized side portion extending transversely outboard of a left longitudinal side edge of the main portion, wherein the left elasticized side portion provides transverse elasticity and comprises a side elastic material to contract and gather at least a portion of the left side portion;

a right elasticized side portion extending transversely outboard of a right longitudinal side edge of the main portion, wherein the right elasticized side portion provides transverse elasticity and comprises a side elastic material to contract and gather at least a portion of the right side portion;

an elasticized waist portion adjacent said waist opening, wherein the elasticized waist portion provides elasticity and comprises a waist elastic material to contract and gather at least a portion of the waist portion, wherein at least a portion of the waist elastic material overlaps with a portion of the left elasticized side portion, wherein at least a portion of the waist elastic material overlaps with the right elasticized side portion, wherein said elasticized waist portion comprises a center waist portion having a contraction rate, an outer side waist portion having a contraction rate, and an inner side waist portion having a contraction rate, wherein the outer side waist portion is transversely outboard the center waist portion, and is contiguous with the seam, wherein the inner side waist portion is between the outer side waist portion and the center waist portion, wherein the contraction rate of the inner side waist portion is less than the contraction rate of the center waist portion, wherein the contraction rate of the outer side waist portion is greater than the contraction rate of the inner side waist portion;

a left barrier leg cuff comprising a barrier elastic material, and extending longitudinally along a left region of the main portion, wherein a longitudinal portion of the left barrier leg cuff overlaps with a portion of the center waist portion and wherein a transverse portion of the left barrier leg cuff overlaps with a portion of the left elasticized side portion; and a right barrier leg cuff comprising a barrier elastic material, and extending longitudinally along a right region of the main portion, wherein a longitudinal portion of the right barrier leg cuff overlaps with a portion of the center waist portion and wherein a transverse portion of the right barrier leg cuff overlaps with a portion of the right elasticized side portion wherein said barrier elastic material of said left barrier leg cuff is disposed inboard of said left longitudinal edge of said absorbent core and wherein said barrier elastic material of said right barrier leg cuff is disposed inboard of said right longitudinal edge of said absorbent core.

8. The disposable pull-on garment of claim 7 further comprising a leg elastic material disposed outboard of a longitudinal edge of said absorbent core.

9. The disposable pull-on garment of claim 7 wherein said elasticized waist portion is disposed onto said left and right barrier leg cuffs.

* * * * *